(12) United States Patent
Auge et al.

(10) Patent No.: US 6,545,039 B1
(45) Date of Patent: Apr. 8, 2003

(54) FACILITATED ADMINISTRATION OF α-LIPOIC ACID OR DERIVATIVES THEREOF

(75) Inventors: Mechthild Auge, Wehrheim (DE); Claudia Wicke, Flörsheim (DE); Robert Hermann, Hanau (DE); Klaus Wessel, Bad Vilbel (DE)

(73) Assignee: Viatris GmbH & Co. KG (DE)

( * ) Notice: Subject to any disclaimer, the term of this patent is extended or adjusted under 35 U.S.C. 154(b) by 0 days.

(21) Appl. No.: 09/708,703

(22) Filed: Nov. 9, 2000

(30) Foreign Application Priority Data

Nov. 11, 1999 (DE) .......................................... 199 54 321

(51) Int. Cl.$^7$ ............................................... A61K 31/21
(52) U.S. Cl. ....................................................... 514/440
(58) Field of Search .......................................... 514/440

(56) References Cited

U.S. PATENT DOCUMENTS

| | | | |
|---|---|---|---|
| 4,411,649 A | | 10/1983 | Kamen |
| 5,445,621 A | | 8/1995 | Poli et al. |
| 5,948,810 A | | 9/1999 | Wessel et al. |
| 5,990,153 A | * | 11/1999 | Wood et al. ................ 514/440 |

FOREIGN PATENT DOCUMENTS

| WO | WO 99/55331 | 11/1999 |
|---|---|---|

* cited by examiner

*Primary Examiner*—Rebecca Cook
(74) *Attorney, Agent, or Firm*—Ann S. Hobbs; Venable

(57) ABSTRACT

Racemic α-lipoic acid or its enantiomers or pharmaceutically acceptable salts, esters or amides thereof can be administrated parenterally at a rate of 50 to 600 mg of active compound, based on racemic α-lipoic acid, per minute.

12 Claims, No Drawings

FACILITATED ADMINISTRATION OF α-LIPOIC ACID OR DERIVATIVES THEREOF

The invention relates to a process for the administration of racemic α-lipoic acid or its enantiomers or pharmaceutically acceptable salts, esters or amides thereof within a certain rate range.

α-Lipoic acid is a naturally occurring antioxidant and a cofactor of the glucose-metabolizing pyruvate dehydrogenase (Packer, L. et al., Free Radicals in Biology & Medicine 19 (2): 227–250; 1995) and is used to a wide extent for the treatment of diabetic polyneuropathy (Ziegler, D. et al., Diabetologia 38: 1425–1433; 1995). Moreover, α-lipoic acid has been used for decades for the treatment of liver disorders (Bode, J. Ch. et al., DMW 112 (9), 349–352; 1987) and fungal intoxications (Brunn, J. et al., Internist. Prax. 19: 475–478, 1979). The molecular mode of action has recently been characterized as that of a diabetes-specific antioxidant (Nagamatsu, M. et al., Diabetes Care 18 (8): 1160–1167; 1995).

Medicaments containing α-lipoic acid are obtainable in the form of tablets for oral assimilation as well as ampoules and ready-to-use infusion devices for infusion or intramuscular injection. According to standard technical information α-lipoic acid injection solution, BfArM 8.3.96, No. Fi44002V.doc, of the Federal Institute for Pharmaceutical Products (BfArM), i.v. injection was previously restricted to low infusion rates and i.m. injection was not recommended. The parenteral products contain water-soluble salts of α-lipoic acid. At present, the trometamine salt, the ethylenediamine salt and the meglumine salt are used. The tolerability is regarded as dose-dependent (Ziegler, et al., loc.cit.). In the above-mentioned information of the BfArM, the physician is explicitly warned against carrying out the administration more rapidly than 50 mg of α-lipoic acid or an equivalent amount of the salt per minute.

Resulting from this, the parenteral administration of α-lipoic acid until now has been dependent on clinical or clinic-like infrastructures in medical practice such as a bed for the infusion and technical assistance during the infusion period. The acceptance of the patient is usually adversely affected by this time-consuming mode of administration. The costs of the administration are increased by the necessity of additional solutions for the dissolution of the active compound or dilution of concentrated solutions. The parenteral administration of the products in general medical practice is nearly impossible under these circumstances and the oral formulations predominate in the case of prescriptions (Rathmann, W. et al., Pharmaepidemiology and Drug Safety 7: 51–57; 1998).

This preference of the oral formulations, however, can only be regarded as suboptimal for the success of treatment in many patients, because the oral formulations have a critical bioavailability with high inter- and intraindividual variations and are associated with additional problems such as the in-vivo interaction with foodstuffs (Gleiter, C. H. et al., Eur. J. Clin. Pharmacol., 50: 513–514, 1996; Hermann, R. et al., Eur. J. Pharm. Sci., 4: 167–174, 1996). Oral formulations are therefore only second choice for reasons of bioavailability.

The aim of the invention is to create a process which is equally easy to carry out in medical practice and is tolerable for the patients and also ensures an optimal bioavailability.

Surprisingly, it has been found that the trometamine salt of racemic α-lipoic acid can be administered at an infusion or injection rate of more than 200 to 1200 mg of active compound, based on α-lipoic acid.

The product can thus be administered in a simple manner as a direct intravenous injection in the course of less than twelve, better still six or three minutes, in fact even within one minute. Clinical or clinic-like infrastructures are no longer necessary. Cost-intensive infusion sets and dilution solutions are likewise unnecessary. Optimal administration of α-lipoic acid with clearly reduced costs is achieved, which can benefit more patients than previously, since the administration can be carried out in any medical practice and the patients agree more willingly.

The process according to the invention can preferably be practised by direct manual i.v. injection but also by rapid infusion using an infusion device or using an automatic infusion pump, e.g a perfusor, which can also be provided with a butterfly needle.

The infusion or injection solution used according to the invention can be withdrawn from ampoules or ready-to-use infusion or injection bottles by syringes, it also being possible to use a butterfly needle for withdrawal from bottles.

The ampoules or bottles have a volume of 4 to 120 ml, preferably 4 to 24 ml, ampoules more likely being in the lower range and bottles in the upper range, and contain 25 to 1200 mg of active compound, preferably 200 to 1200 mg of active compound, based on α-lipoic acid.

The following examples illustrate the invention without restricting it.

Pharmaceutical Example

Ampoules with 250 mg of racemic α-lipoic acid as trometamine salt in 10 ml 250 g of racemic α-lipoic acid are dissolved with stirring in a mixture of 9 liters of water for injection and 200 g of 1,2-propylene glycol together with 352.3 g of trometamine (2-amino-2-(hydroxymethyl)-1,3-propanediol). The solution is made up to 10 liters with water for injection and then filtered through a membrane filter of pore width 0.2 $\mu$m using a glass fiber prefilter. 10 ml of the filtrate is dispensed into sterilized 10 ml ampoules under aseptic conditions.

An ampoule contains 250 mg of racemic α-lipoic acid as trometamine salt in 10 ml of injection solution.

Clinical Examples

In a study with 12 volunteer, healthy subjects (6 male and 6 female), 24 ml of the above infusion solution, which contained 952.8 mg of the trometamine salt of α-lipoic acid (corresponds to 600 mg of α-lipoic acid), were administered intravenously within 6, 3 or 1 min, i.e., at an infusion rate of 100 mg/min, 200 mg/min or 600 mg/min. The following results were obtained here.

1. All infusion rates used, even those clearly lying above the present threshold of 50 mg/min, were excellently tolerated by the subjects.
2. In the three infusion schemes, peak plasma concentrations ($C_{max}$) of 60.2, 76.2 or 63.0 $\mu$g/ml were achieved for the infusion rates of 100, 200 or 600 mg/min. At the rate previously regarded as a limit for the tolerability, a value of 20–25 $\mu$g/ml is established. The invention shows that even with $C_{max}$ values in the range up to approximately 80 $\mu$g/ml, i.e. clearly above the mentioned value of 20–25 $\mu$g/ml, the safety and tolerability in the clinical administration of α-lipoic acid is not restricted.
3. While the comparison of the present study with earlier experiments shows that at infusion rates of between 17 and 100 mg/min the maximum plasma concentration ($C_{max}$) increases progressively relative to the infusion rate, this is surprisingly no longer the case on a further increase of the infusion rate from 100 to 600 mg/min, since the measured $C_{max}$ values do not differ significantly for 100 and 600 mg/min (60.2 vs. 63.0 µg/ml).

On the basis of the results of the study, the previous assumptions about the intravenous administration of α-lipoic acid must be revised. Possibly, the unexpectedly good tolerability described under items 1 and 2 can be explained at least partially by the pharmacokinetic observation under item 3.

What is claimed is:

1. A method of intravenously injecting a solution comprising racemic α-lipoic acid or an enantiomer or pharmaceutically acceptable salt, ester or amide thereof as active compound, wherein said solution is administered to a human patient at a rate of 100 to 600 mg of said active compound per minute.

2. The method according to claim 1, wherein the rate is 200 to 600 mg per minute.

3. The method according to claim 1, wherein said solution is provided in the form of an ampoule or ready-to-use infusion or injection bottle.

4. The method according to claim 1, wherein said solution is administered by means of an infusion device or a perfusor.

5. The method according to claim 4, wherein the infusion device or perfusor is provided with a butterfly needle.

6. The method according to claim 1, wherein the preparation is administered intravenously by means of a syringe.

7. The method according to claim 1, wherein the solution has a volume of 4 to 120 ml.

8. The method according to claim 7, wherein the solution contains 25 to 1200 mg of said active compound.

9. The method according to claim 1, wherein the solution has a volume of 4 to 24 ml.

10. The method according to claim 9, wherein said solution contains 200 to 1200 mg of said active compound.

11. The method according to claim 1, wherein said solution is a medicament.

12. The method according to claim 1, wherein said solution is a food supplement for parenteral nutrition.

* * * * *